US008142795B2

(12) United States Patent
Françon et al.

(10) Patent No.: US 8,142,795 B2
(45) Date of Patent: Mar. 27, 2012

(54) STABILIZER AND VACCINE COMPOSITION COMPRISING ONE OR MORE LIVE ATTENUATED FLAVIVIRUSES

(75) Inventors: Alain Françon, Bessenay (FR); Olivier Brass, Caluire & Cuire (FR); Pierre Chouvenc, Lyons (FR); Amandine Leleu, Lyons (FR)

(73) Assignee: Sanofi Pasteur, Lyons (FR)

( * ) Notice: Subject to any disclaimer, the term of this patent is extended or adjusted under 35 U.S.C. 154(b) by 144 days.

(21) Appl. No.: 12/500,156

(22) Filed: Jul. 9, 2009

(65) Prior Publication Data

US 2010/0015180 A1 Jan. 21, 2010

Related U.S. Application Data

(60) Provisional application No. 61/097,013, filed on Sep. 15, 2008.

(30) Foreign Application Priority Data

Jul. 9, 2008 (EP) .................................... 08305390

(51) Int. Cl.
*A61K 39/12* (2006.01)
*A61K 39/295* (2006.01)
*C12N 7/00* (2006.01)

(52) U.S. Cl. ................................. 424/218.1; 435/235.1

(58) Field of Classification Search ........................ None
See application file for complete search history.

(56) References Cited

U.S. PATENT DOCUMENTS

| | | | | |
|---|---|---|---|---|
| 3,162,019 | A | 12/1964 | Porter et al. | |
| 3,313,032 | A | 4/1967 | Malecki | |
| 3,431,655 | A | 3/1969 | Grover et al. | |
| 3,655,838 | A | 4/1972 | Price et al. | |
| 4,211,015 | A | 7/1980 | Adams et al. | |
| 4,500,512 | A | 2/1985 | Barme | |
| 5,036,673 | A | 8/1991 | Miller et al. | |
| 5,307,640 | A | 5/1994 | Fawzy et al. | |
| 5,897,852 | A * | 4/1999 | Wilderbeek et al. | 424/10.3 |
| 6,210,683 | B1 | 4/2001 | Burke et al. | |
| 6,231,860 | B1 * | 5/2001 | Fanget et al. | 424/184.1 |
| 6,589,522 | B1 | 7/2003 | Galler et al. | |
| 6,696,281 | B1 | 2/2004 | Chambers et al. | |
| 6,862,890 | B2 | 3/2005 | Williams et al. | |
| 6,903,065 | B2 | 6/2005 | Nyssen et al. | |
| 6,962,708 | B1 | 11/2005 | Chambers et al. | |
| 2004/0052818 | A1 | 3/2004 | Heinz et al. | |
| 2008/0014219 | A1 | 1/2008 | Barban et al. | |
| 2008/0060213 | A1 | 3/2008 | Gehrmann et al. | |
| 2008/0085288 | A1 | 4/2008 | Guy et al. | |
| 2008/0131460 | A1 | 6/2008 | Guy et al. | |

FOREIGN PATENT DOCUMENTS

| | | |
|---|---|---|
| EP | 0 065 905 B1 | 10/1984 |
| EP | 0 799 613 A1 | 10/1997 |
| EP | 1 159 968 B1 | 10/2008 |
| GB | 1 559 920 | 1/1980 |
| WO | WO 93/06214 | 4/1993 |
| WO | WO 96/36317 | 11/1996 |
| WO | WO 96/40933 | 12/1996 |
| WO | WO 98/37911 | 9/1998 |
| WO | WO 00/57904 | 10/2000 |
| WO | WO 00/57908 | 10/2000 |
| WO | WO 00/57909 | 10/2000 |
| WO | WO 00/57910 | 10/2000 |
| WO | WO 01/60847 | 8/2001 |
| WO | WO 02/066621 | 8/2002 |
| WO | WO 02/072835 | 9/2002 |
| WO | WO 02/095075 | 11/2002 |
| WO | WO 02/102828 | 12/2002 |
| WO | WO 03/101397 | 12/2003 |
| WO | WO 03/102166 | 12/2003 |
| WO | WO 03/103571 | 12/2003 |
| WO | WO 2004/045529 | 6/2004 |
| WO | WO 2005/082020 | 9/2005 |
| WO | WO 2006/134433 | 12/2006 |
| WO | WO 2006/134443 | 12/2006 |
| WO | WO 2007/056847 | 5/2007 |
| WO | WO 2008/057550 | 5/2008 |

OTHER PUBLICATIONS

Adebayo et al., "Stability of 17D Yellow Fever Virus Vaccine Using Different Stabilizers," Biologicals 26:309-316, 1998.
Barme et al., "Thermostabilisation du Vaccin Antiamiril 17D Lyophilisé. I. Essai de Substances Protectrices" (Thermostabilization of the Lyophilized Yellow Fever Vaccine 17-D. II. Pilot Lots Prepared Under Conditions of Industrial Production), J. Biol. Stand. 12:435-442, 1984.
Brandenberger et al., "A New Multinozzle Encapsulation/Immobilization System to Produce Uniform Beads of Alginate." J. Biotechnology 63:73-80, 1998.
Galler et al., "Genetic Variability Among Yellow Fever Virus 17D Substrains," Vaccine 16:1024-1028, 1998.
Gotoh et al. "Mass-production of Biocatalyst-entrapping Alignate Gel Particles by a Forced Oscillation Method," Chemical Engineering Communications 120:73-84, 1993.
Hulst et al., "A New Technique for the Production of Immobilized Biocatalyst in Large Quantities," Biotechnol. Bioeng. 27:870-876, 1985. Lai et al., "Chimeric Flaviviruses: Novel Vaccines Against Dengue Fever, Tick-Borne Encephalitis, and Japanese Encephalitis," Adv. Virus Res. 61:469-509, 2003.
Rayleigh, "On the Instability of Jets," Proc. Lond. Math. Soc. 10:4-12, 1878.
Rice et al., "Nucleotide Sequence of Yellow Fever Virus: Implications for Flavivirus Gene Expression and Evolution," Science 229: 726-733, 1985.
Seifert et al., "Production of Small Monodispersed Alginate Beads for Cell Immobilization," Biotechnol. Prog. 13:562-568, 1997.
Sindayihebura et al., "Experimental Study of Thin Liquid Film Ultrasonic Atomization," Ex HFT 97:1-7, 1997.
Sood et al., "Study on the Stability of 17D-204 Yellow Fever Vaccine Before and After Stabilization," Vaccine 11:1124-1128, 1993.
Theiler et al., "The Use of Yellow Fever Virus Modified by in vitro Cultivation for Human Immunization," J. Exp. Med. 65:787-800, 1937.
Toriniwa et al., "Long-Term Stability of Vero Cell-Derived Inactivated Japanese Encephalitis Vaccine Prepared Using Serum-Free Medium," Vaccine 26:3680-3689, 2008.

International Search Report from International Application No. PCT/EP2009/004980, dated Oct. 2, 2009 (date of completion of search) and Oct. 13, 2009 (date of mailing of report).

Written Opinion from International Application No. PCT/EP2009/004980, dated Oct. 2, 2009 (date of completion of the opinion) and Oct. 13, 2009 (date of mailing of report).

* cited by examiner

*Primary Examiner* — Mary E Mosher

(74) *Attorney, Agent, or Firm* — Clark & Elbing LLP

(57) ABSTRACT

The present invention relates to stabilizers for compositions, including immunogenic compositions, such as vaccine compositions, comprising one or more live attenuated flaviviruses, to bulk vaccine compositions stabilized with these stabilizers, particularly dry vaccine compositions prepared from these bulk vaccine compositions, and to methods for stabilizing one or more live attenuated flaviviruses.

28 Claims, 2 Drawing Sheets

Figure 1: Production of the dry vaccine composition according to the present invention in the form of uniform particles or of beads (microbeads)

Figure 2: Dry vaccine composition according to the present invention in the form of uniform particles or of beads (microbeads)

STABILIZER AND VACCINE COMPOSITION COMPRISING ONE OR MORE LIVE ATTENUATED FLAVIVIRUSES

This application claims priority from European Patent Application No. 08305390.0, filed Jul. 9, 2008, and also claims benefit of U.S. Provisional Patent Application No. 61/097,013, filed Sep. 15, 2008, the contents of each of which are incorporated herein by reference.

The present invention relates to a stabilizer for vaccine compositions comprising one or more live attenuated flaviviruses, to a bulk vaccine composition stabilized with this stabilizer, particularly a dry vaccine composition prepared from this bulk vaccine composition, and to a method for stabilizing one or more live attenuated flaviviruses.

Flaviviruses are a genus of viruses of the family Flaviviridae. This group comprises the dengue (DEN) virus, the yellow fever (YF) virus, the Saint Louis encephalitis virus, the Japanese encephalitis (JE) virus, and the West Nile (WN) virus. Among these viruses, some are unstable.

In the context of the present invention, the term "flavivirus" is intended to mean any virus of the family Flaviviridae which is pathogenic for animals, including mammals, in particular flaviviruses which are pathogenic for humans. By way of nonlimiting examples, mention may be made of the following flaviviruses: dengue (DEN) virus serotypes 1, 2, 3, and 4, Japanese encephalitis (JE) virus, yellow fever (YF) virus, and West Nile (WN) virus.

The term "live" is used in its conventional meaning, a live virus is a virus that has not been inactivated, i.e., a virus capable of replicating on permissive cells.

A live attenuated flavivirus is a flavivirus which does not induce the disease caused by the corresponding wild-type virus in animals or humans and which is capable of inducing a specific immune response.

By way of nonlimiting examples of live attenuated flaviviruses that can be used with the stabilizer according to the invention, mention may be made of attenuated viral strains such as the JEV strain SA-14-14-2, the YF vaccine strains such as the YF strain described in U.S. Pat. No. 6,589,522, the dengue viral strains described in application WO 2006/134433 A1, in particular the VDV1 strain, the strains described in application WO 2006/134443 A1, in particular the VDV2 strain; the strains described, for example, in applications: WO 02/66621, WO 00/57904, WO 00/57908, WO 00/57909; WO 00/57910, WO 02/95075 and WO 02/102828, and the strains DEN-1 16007/PDK13, also called "LAV1," DEN-2 16681/PDK53, also called "LAV2," and LAV4, which are described in patent application EP1 159 968 A.

The VDV1 strain is a strain obtained from a wild-type DEN-1 strain 16007 having undergone 11 passes on PDK cells (DEN-1 16007/PDK11) and which was subsequently amplified on Vero cells at 32° C., and the RNA of which was purified and transfected into Vero cells. The VDV-1 strain has 14 additional mutations compared with the vaccine strain DEN-1 16007/PDK13 (13 passes on PDK—Primary Dog Kidney cells). The complete sequence and also a preparation method and the characterization of the VDV-1 strain are given in application WO 2006/134433 A1. Said strain can be readily reproduced based on this teaching.

The VDV-2 strain is a strain obtained from a wild-type DEN-2 strain 16681 having undergone 50 passes on PDK cells (DEN-2 16681/PDK50), plaque-purified and the RNA of which was extracted and purified before being transfected into Vero cells. The VDV-2 strain was subsequently obtained by plaque-purification and amplification on Vero cells. The VDV-2 strain has 10 additional mutations compared with the vaccine strain DEN-2 16681/PDK53 (53 passes on PDK cells). The complete sequence and also a preparation method and the characterization of the VDV-2 strain are given in application WO 2006/134443 A1. Said strain can be readily reproduced based on this teaching.

Among live attenuated flaviviruses that can be used with the stabilizer according to the invention, mention may also be made—in a nonlimiting manner—of chimeric viruses such as: the chimeric viruses described, for example, in international application WO 93/06214 and also the ChimeriVax®. The term "ChimeriVax®" or "CYD" denotes a chimeric yellow fever (YF) virus which comprises the backbone of a YF virus in which the sequences encoding the premembrane and envelope proteins have been replaced with the corresponding sequences of any strain of a different flavivirus, for instance of a dengue (DEN) virus (e.g., of any of serotypes 1-4), of a Japanese encephalitis (JE) virus, or of a West Nile (WN) virus. The construction of these ChimeriVax® has been described in detail in international patent applications WO 98/37911 and WO 03/101397 (also see, e.g., U.S. Pat. Nos. 6,962,708 and 6,696,281), to which reference may be made for a precise description of the method for preparing them. A review on live attenuated chimeric flaviviruses that can be used in the context of the present invention is given by C.-J. Lai and T. P. Monath in "Advances in Virus Research", (2003) vol. 61, pages 469 to 509.

A chimeric YF virus containing the prM and E sequences of a dengue serotype 1 strain (DEN-1) is thus termed CYD-1 or CYD DEN1. A chimeric YF virus containing the prM and E sequences of a DEN-2 strain is termed CYD-2 or CYD DEN2. A chimeric YF virus containing the prM and E sequences of a DEN-3 strain is termed CYD-3 or CYD DEN3. A chimeric YF virus containing the prM and E sequences of a DEN-4 strain is termed CYD-4 or CYD DEN4. A dengue chimeric virus may, for example, be ChimeriVax® DEN-1, in particular, a YF17D/DEN-1 virus, or else a ChimeriVax® DEN-2, in particular a YF17D/DEN-2 virus, a ChimeriVax® DEN-3, in particular a YF17D/DEN-3 virus or a ChimeriVax® DEN-4, in particular a YF17D/DEN-4 virus. The chimeras described in the examples were generated by using the prM and E sequences derived from the DEN 1 PUO359 (TVP1140), DEN2 PUO218, DEN3 PaH881/88, and DEN4 1228 (TVP 980) strains.

Preferably, the chimeric YF virus comprises the backbone of an attenuated yellow fever strain YF17D (Theiler M, and Smith H H, 1937, J. Exp. Med. 65:767-786) (e.g., YF17D/DEN-1, YF17D/DEN-2, YF17D/DEN-3, YF17D/DEN-4 viruses). Examples of YF17D strains that can be used include YF17D204 (YE-Vax®, Sanofi-Pasteur, Swiftwater, Pa., USA; Stamaril®, Sanofi-Pasteur, Marcy l'Etoile, France; ARILVAX™, Chiron, Speke, Liverpool, UK; FLAVIMUN®, Berna Biotech, Bern, Switzerland; YF17D-204 France (X15067, X15062); YF17D-204,234 US (Rice et al., 1985, Science 229:726-733), or else related strains YF17DD (Genbank accession number U17066), YF17D-213 (Genbank accession number U17067), and the YF17DD strains described by Gaiter et al. (1998, Vaccines 16(9/10):1024-1028). Any other attenuated yellow fever virus strain that can be used in humans may be used for the construction of the chimeras. These same yellow fever strains may be used as such with the stabilizer according to the invention for the preparation of a composition that can be used in the context of an immunization against yellow fever.

The chimeras in which the vector is a dengue virus, as described, for example, in patent applications WO 96/40933 and WO 01/60847, can also be used with the stabilizer according to the invention.

Different embodiments of chimeric viruses are also described in applications WO 02/102828; WO 03/103571; WO 02/072835; WO 2004/045529; and WO 2005/082020, which viruses can also be used with the stabilizer according to the present invention.

Furthermore, the chimeric vectors described above in which the heterologous sequences inserted are sequences as described, for example, in application WO 03/102166 can also be used in the context of the invention.

The chimeric viruses have the particularity of exhibiting the characteristics of the live attenuated viruses as defined above. It is therefore possible to use, in the context of the invention, any chimeric virus expressing the envelope protein or one or more epitopes of one or more envelope protein(s) of one or more flaviviruses and inducing a specific immune response comprising antibodies which neutralize the strain, or at least one of the strains, from which the envelope protein or said epitope is derived.

In the context of the present invention, the term "bulk vaccine composition" is intended to mean a composition which exits the final stage of the antigen production, purified or nonpurified, monovalent, or after multivalent mixing.

In the context of the present invention, the term "a dry vaccine composition" is intended to mean a composition of which the residual water content is less than or equal to 3%, and which is ready to be reconstituted with an aqueous solution in order to be used as a vaccine or directly in dry particulate form.

The term "spray-freeze-drying" is understood to mean the spraying with a fluid in a cryogenic environment, followed by freeze-drying of the frozen particles obtained.

The term "foam-drying" is understood to mean the drying, in the form of a glassy foam by evaporation of water, of a concentrated solution.

The term "freeze-foam-drying" is understood to mean the drying, in the form of a glassy foam by sublimation of ice, of a pre-frozen solution, at a temperature below the glass transition temperature and the matrix collapse temperature.

The aqueous compositions of flaviviruses do not allow good viral stability in the long term and at a temperature above 5° C. By way of example, the bulk aqueous compositions of the YF-DEN (yellow fever-dengue) chimera lose more than 4 log, stabilized in liquid after storage for 1 day at 37° C. Now, this thermolability represents a serious problem in subtropical YF-endemic countries where transport under cold-chain conditions is difficult.

In the 1970s-1980s, freeze-dried yellow fever vaccines exhibited a serious thermostability problem (storage: 6 months at +5° C.). These freeze-dried vaccines without stabilizer degrade very rapidly when they are exposed to a temperature above 20° C. Efforts were made to improve the stabilization of freeze-dried yellow fever vaccine compositions (loss in 7 days at 37° C., nonstabilized vaccine: 0.87 log, stabilized vaccine: 0.24 log). The stabilizer developed for yellow fever (M. Barme and C. Bronnert, 1984, J. Biol. Standardization, 12:435), used for the chimeric YF-DEN (yellow fever-dengue) vaccine is found to be ineffective (loss in 7 days at 37° C. for serotype 1: 2.1 log; for serotype 2: 1.3 log; for serotype 3: 1.4 log; for serotype 4: 1.9 log). More recently, A. A. Adebayo et al. (Biologicals, 1998, 26:309-316) proposed stabilizers for a freeze-dried 17D yellow fever vaccine and they note a loss of live and effective 17D virus of 50% (0.3 log) after storage at 37° C. for 28 days. Also, very recently human serum albumin (HSA) as a stabilizer combined with sugars as bulking agents and a buffer for lyophilized compositions containing live attenuated flaviviruses have been proposed in WO 2008/057550.

The present invention makes it possible to solve the problem of the stabilization of flavivirus vaccine compositions, particularly chimeric flavivirus vaccines, in particular, the YF-DEN (yellow fever-dengue) chimera.

The present invention therefore relates to a stabilizer for compositions comprising one or more live attenuated flaviviruses (e.g., immunogenic compositions, such as vaccine compositions), characterized in that it comprises, in an aqueous solution without proteins of animal origin and without added salts having divalent cations, a buffer,
2.5% to 6.5% of sorbitol,
2.5% to 13% of sucrose,
0 to 7.5% of trehalose and/or 0 to 7.5% of any other disaccharide or trisaccharide,
0.2% to 0.5% of urea,
0.8% to 2.5% of an amino acid mixture comprising arginine (Arg), cystine (Cys-Cys), histidine (His), isoleucine (Ile), leucine (Leu), lysine (Lys), methionine (Met), phenylalanine (Phe), threonine (Thr), tryptophan (Trp), tyrosine (Tyr), valine (Val), alanine (Ala), asparagine (Asn), aspartic acid (Asp), glutamic acid (Glu), glycine (Gly), proline (Pro) and serine (Ser).

The stabilizer according to the present invention may contain one or more buffers chosen from the group comprising TRIS (tris(hydroxymethyl)amino-methane), HEPES (2-(4-(2-hydroxyethyl)-1-piperazinyl)ethanesulfonic acid) and potassium phosphate and/or sodium phosphate, the TRIS for example at a concentration of from 5 to 10 mM, the HEPES for example at a concentration of from 7.5 to 20 mM.

More specifically, the stabilizer according to the present invention comprises
3.8% (w/v) of sorbitol,
7.5% (w/v) of sucrose,
5.5% (w/v) of trehalose,
0.25% (w/v) of urea and
1.5% (w/v) of the amino acid mixture.

The present invention also relates to stabilized bulk aqueous compositions (e.g., immunogenic compositions, such as vaccine compositions), which comprise one or more live attenuated flaviviruses and the stabilizer described above according to the invention.

The composition according to the present invention may comprise one or more serotypes of live attenuated dengue (DEN) viruses and/or of live attenuated yellow fever (YF) viruses and/or of live attenuated West Nile (WN) virus disease viruses and/or of live attenuated Japanese encephalitis (JE) viruses.

Variations of the present invention comprise one or more live attenuated chimeric flaviviruses, for example one or more serotypes of a chimeric YF-DEN (yellow fever-dengue) virus, of a chimeric YF-WN (yellow fever-West Nile virus) virus and/or of a chimeric YF-JE (yellow fever-Japanese encephalitis) virus.

The present invention also relates to a method for stabilizing one or more live attenuated flaviviruses. At the final stage in the production of the live attenuated flaviviruses (for example, culture on Vero cells, infection and viral culture followed by purification in one or more steps), the purified or nonpurified and concentrated or nonconcentrated viral harvest comprising a live attenuated flavivirus is diluted by adding stabilizer so as to obtain the final concentrations of the stabilizer according to the present invention in order to obtain a stabilized bulk aqueous vaccine composition according to the present invention. Multivalent compositions are obtained by mixing purified or nonpurified, concentrated or nonconcentrated, and stabilized viral harvests.

The stabilization method according to the present invention may also comprise drying the aqueous composition by a method selected from the group of foam-drying, spray-drying or freeze-foam-drying, for example drying the aqueous composition by the freeze-drying method or by the spray-freeze-drying method. By choosing the freeze-drying or spray-freeze-drying method, the stabilization method according to the present invention may be modified by freezing the aqueous solution in the form of uniform particles or beads in a first step and by drying the frozen uniform particles or beads in a second step in order to obtain a stabilized dry product in the form of uniform particles or of beads. The generation of beads can preferably be carried out under sterile conditions. The uniform particles or the beads (or more concretely the microbeads) are generated by freezing drops of the aqueous composition according to the present invention either by dropping into a very cold gas (evaporated liquid nitrogen) or by direct dropping into a cryogenic liquid (for example liquid nitrogen). The preparations of the frozen uniform particles or frozen beads from an aqueous solution or liquid are illustrated in Price et al. (U.S. Pat. No. 3,655,838), Adams et al. (U.S. Pat. No. 4,211,015), A. A. Fawzy et al. (U.S. Pat. No. 5,307,640), R. O. Williams III et al. (U.S. Pat. No. 6,862,890 B2), P. F. Herbert et al. (WO 96/36317) and P.-R. Nyssen et al. (U.S. Pat. No. 6,903,065 B2). The freezing of the droplets can e.g. also be achieved in that the stabilized bulk aqueous vaccine composition according to the present invention is prilled in order to generate calibrated droplets which diameter ranges from 100 μm to 1500 μm, with a very narrow size distribution. These droplets fall in a cryogenic chamber in which low temperature is maintained by a freezing medium, either by direct injection/nebulization of liquid nitrogen or by flowing counter currently a very cold gas such as nitrogen, $CO_2$ or air. The droplets freeze during their fall in order to form calibrated frozen particles.

Prilling, also known as laminar jet break-up technique, is a well known technique to generate calibrated droplets of liquid commonly used in the field of biocatalysts and living cells immobilization (Hulst et al., 1985. A new technique for the production of immobilized biocatalyst and large quantities. Biotechnol. Bioeng. 27:870-876; Gotoh et al., 1993. Mass production of biocatalyst-entrapping alginate gel particles by a forced oscillation method. Chem. Eng. Commun. 120:73-84; Seifert and Philips, 1997. Production of small, monodispersed alginate beads for cell immobilization. Biotechnol. Prog. 13:562-568). Lord Rayleigh was the first to analyze instability of capillary jets coming out of a nozzle and to propose a model to describe it (Rayleigh L, 1978. On the stability of jets. Proc. London Math. Soc. 10:4-13) for Newtonian fluids. Weber (Weber C, 1931. Zum Zerfall eines Flüssigkeitsstrahles. Z. Angew. Math. Mech. 11:136-154) extended the analysis including the effect of the viscosity. The optimal wavelength for the fastest growing disturbance and jet beak-up is given by:

$$\lambda_{opt} = \pi \cdot \sqrt{2} \cdot d_j \cdot \sqrt{1 + \frac{3\eta}{\rho\sigma d_j}}$$

Where $\lambda_{opt}$ is the optimal wave-length for jet break-up, $d_j$ is the diameter of the jet, $\eta$ is the viscosity of the fluid, $\rho$ is the density of the fluid and $\sigma$ is the surface tension of the fluid. The diameter d of the droplets formed can be calculated by:

$$d = \sqrt[3]{\sqrt{1.5 \cdot d_j^2 \cdot \lambda_{opt}}}$$

The frequency f to apply to the fluid to achieve the desired results is related to the jet velocity (and therefore the flow rate of the fluid) $u_j$ and the wavelength by:

$$\lambda = \frac{u_j}{f}$$

Therefore, optimal conditions can be calculated knowing process parameters and fluid characteristics. However, a range of frequencies and jet velocities exist to form uniform droplets depending on the nozzle diameter, rheology of the fluid and surface tension (Meesters G., 1992. Mechanisms of droplet formation. Delft University Press, Delft, N L). Suitable working frequencies can be also be determined experimentally by visual assessment of the stability of the droplet formation. Standard prilling equipments are equipped with light stroboscope to observe the droplet formation: for a given product and given working conditions, one can adjust manually the frequency until observing a stable and still droplets chain with this stroboscope light. Moreover, multinozzle systems have been developed for aseptic prilling applications (Brandenberger H. et al, 1998, A new multinozzle encapsulation/immobilization system to produce uniform beads of alginates. J. Biotechnol. 63:73-80). In conclusion, working frequencies can be determined both theoretically and experimentally depending on the available tools and knowledge of the product.

The prilling process is adapted to viscous liquids. The maximum acceptable viscosity according to current suppliers is approximately 300 mPa·s. The temperatures in the process tubing and in the nozzle have to be controlled in order to avoid solvent crystallization before droplet formation. The person skilled in the art of formulation will adjust different excipient concentrations in the product in order to avoid non-controlled crystallization and viscosities above the given limit, taking into account eventual interactions between excipients.

The stabilized bulk aqueous vaccine composition according to the present invention can be prilled in order to generate calibrated droplets the diameter of which ranges from 100 μm to 1500 μm, with a very narrow size distribution. These droplets fall in a cryogenic chamber in which low temperature is maintained either by direct injection/nebulization of liquid nitrogen or by flowing counter currently a very cold gas such as nitrogen, $CO_2$ or air. The droplets freeze during their fall in order to form calibrated frozen particle. The minimum falling height to freeze the droplets (i.e. ice crystals formation that solidifies the pellets) can be minimized by limiting super-cooling. Super-cooling can be reduced by seeding ice nucleation in the droplets either by contact with liquid nitrogen fog or droplets (direct injection of liquid nitrogen in the chamber) or with microscopic ice crystals (direct nebulization of water or superheated steam in the cold chamber).

Other techniques are known in the art for obtaining calibrated droplets, such as ultrasonic atomization (Sindayihebura D., Dobre M., Bolle L., 1997, Experimental study of thin liquid film ultrasonic atomization. ExHFT'97, Bruxelles), and, subsequently, calibrated frozen particles or, as known from the food industry, by means of a particular freezing drum as disclosed in U.S. Pat. No. 5,036,673.

The aqueous solution frozen in the form of uniform particles or of beads (microbeads) is subsequently freeze-dried.

Under the laminar-flow ceiling, the microbeads are distributed on trays. The steps that were carried out are described below:

Precooling of the shelves of the freeze-drier to −50° C.

Adhesion of the labels to the trays for tray identification.

Cooling of handling tools and of the trays to −50° C. on the shelves of the freeze-drier for approximately one hour.

The frozen microbeads are subsequently transferred from their containers into the trays. The trays are subsequently agitated so that the beads are homogeneously distributed. The beads distributed on the tray are subsequently freeze-dried. These uniform particles or beads (microbeads) of the stabilized dry product emerging from this process have a diameter of approximately 100 µm to 1500 µm, more particularly a diameter of approximately 500 µm to 1000 µm.

Methods and apparatuses for carrying out the freezing of the solutions in the form of frozen uniform particles or beads, followed by drying in order to obtain a dry product in the form of uniform particles or of beads (microbeads), are illustrated for example in W. L. Porter et al. (U.S. Pat. No. 3,162,019), K. M. Gover et al. (U.S. Pat. No. 3,431,655), G. J. Malecki (U.S. Pat. No. 3,313,032), K. D. Heck et al. (DE 26 59 546 A1), A. T. M. Wilderbeek (EP 0 799 613 A1) and D. Gehrmann et al. (U.S. Patent Application Publication No. 2008/0060213 A1).

The present invention also relates to a dry vaccine composition obtained by drying the stabilized bulk composition according to the present invention. This dry vaccine composition can be characterized in that the composition is present in the form of uniform particles or of beads. This dry vaccine composition in the form of uniform particles or of beads can be characterized in that each particle or each bead contains a mixture of various live attenuated and/or chimeric live attenuated flaviviruses. This dry vaccine composition in the form of uniform particles or of beads can also be characterized in that each particle or each bead contains live attenuated and/or chimeric live attenuated flaviviruses of a single type.

The present invention also relates to a method for preparing a vaccine, comprising the step of reconstituting the dry vaccine composition obtained by drying the stabilized bulk composition according to the present invention, which may or may not be in the form of uniform particles or of beads (microbeads), with an aqueous solution.

The present invention also relates to a flaviviral vaccine kit comprising a first container containing the dry vaccine composition according to the present invention and a second container containing an aqueous solution for reconstituting the vaccine. This kit can be characterized in that the first container contains a mixture of the various vaccine compositions, each particle or each bead containing live attenuated and/or chimeric live attenuated flaviviruses of a single type.

BRIEF DESCRIPTION OF THE DRAWINGS

FIG. 1 illustrates a method for producing freeze-dried microbeads (see Example 6). The figure illustrates the production of a dry vaccine composition according to the present invention in the form of uniform particles or of beads (microbeads). The following steps are shown: (1&2) formulation, prilling/freezing, (3) BULK drying/freeze-drying, and (4) dry filling.

FIG. 2 illustrates a dry vaccine composition according to the present invention in the form of uniform particles or of beads (microbeads) (see Example 6).

EXAMPLES

Example 1

Preparation of a Stabilized Chimeric Yellow Fever-Dengue Bulk Aqueous Vaccine Composition The monovalent composition was prepared by mixing the chimera YF-DEN, serotype 1, 2, 3, or 4 (CYD-1, -2, -3, or -4) with the stabilizer, so as to obtain the ad hoc stabilizing excipient concentrations. The multivalent composition is obtained by mixing the monovalent compositions.

Each purified monovalent vaccine composition was stabilized with the stabilizer of the present invention and filtered, homogenized, aliquoted and then stored in the frozen aqueous form at a temperature below its glass transition temperature.

Each monovalent vaccine composition was thawed with stirring and the volume of each vaccine composition, to be added to the final mixture in order to prepare the bivalent, trivalent and tetravalent vaccine compositions in target final concentrations was determined according to the following calculation:

$$BulkVolume \text{ (ml)} = \frac{10^{target\ titer/dose} \times \text{volume } BFP \text{ (ml)}}{\frac{10^{bulk\ titer/ml} \times \text{distribution volume}}{\text{vial (ml)}}}$$

BFP signifies Bulk Final Product or mono- or multivalent vaccine composition.

The calculated target volume of each aqueous vaccine composition was sampled and the rest of the volume of monovalent vaccine composition was refrozen. The volumes of the monovalent vaccine compositions were mixed with the stabilizer of the present invention, so as to obtain the target final concentrations and the target volumes. The mixture was homogenized by stirring for 20 minutes at a temperature of 5° C. and filtered sterilely before freezing or drying of the mixture. The mixture had a temperature of 5° C. during the standing periods.

The vaccine composition was prepared by mixing one, two, three, or four bulk monovalent compositions of the chimeric yellow fever-dengue (CYD) viruses with the stabilizer of the present invention, before freezing or drying of the monovalent, bivalent, trivalent, and tetravalent bulk mixture so as to obtain the final compositions in concentrations of chosen target in log/ml. The concentrations may be either equivalent between each monovalent vaccine composition, or different according to the chosen targets.

Example 2

Preparation of a Stabilized Chimeric Yellow Fever-Dengue Bulk Freeze-Dried Vaccine Composition The aqueous monovalent, bivalent, trivalent or tetravalent vaccine composition was obtained according to the description of Example 1. This mixture, stirred and at a temperature of 5° C., was dispensed in an able and reproducible manner at a rate of 0.3 ml per vial, for a period of time necessary for the loading of an industrial freeze-drier. The vials were subsequently loaded onto trays identified by labels in the freeze-drier, the shelves of which were precooled to 5° C. The vials comprising the aqueous vaccine composition at the final target titer were freeze-dried according to the freeze-drying cycle described hereinafter. The vials were frozen to a temperature of −50° C. Once the target temperature had been reached, the frozen vaccine composition included in each vial was sublimated for 16.5 h, with a pressure of 50 μbar for the primary sublimation phase and a shelf temperature of −28° C. The secondary desiccation was carried out at 50 μbar and 30° C. for 5 h. The freeze-dried vials were subsequently stoppered in the freeze-drier by shelf pressure, under vacuum or under partial nitrogen pressure. The vials were unloaded and crimped, labeled, and then stored at a temperature of 5° C.

Example 3

Stability of the Freeze-Dried, Stabilized Chimeric Yellow Fever-Dengue Bulk Tetravalent Vaccine Composition, According to Example 1 and 2

The stabilized, aqueous chimeric yellow fever-dengue bulk tetravalent vaccine composition was stabilized with the stabilizer of the present invention at the target concentration of 6 log/ml, before freeze-drying each vial into which 0.3 ml had been dispensed. The percentage of excipients of the stabilized tetravalent vaccine composition is indicated in Table 1 below:

TABLE 1

Percentage of excipients

| EXCIPIENTS | % |
|---|---|
| L arginine hydrochloride | 1.021 |
| L cystine | 0.012 |
| L histidine | 0.008 |
| L isoleucine | 0.026 |
| L leucine | 0.026 |
| L lysine hydrochloride | 0.037 |
| L methionine | 0.008 |
| L phenylalanine | 0.017 |
| L threonine | 0.024 |
| L tryptophan | 0.004 |
| L tyrosine | 0.018 |
| L valine | 0.024 |
| L alanine | 0.009 |
| L asparagine | 0.015 |
| L aspartic acid | 0.013 |
| L glutamic acid | 0.015 |
| Glycocol | 0.008 |
| L proline | 0.012 |
| L serine | 0.011 |
| Sucrose | 7.500 |
| D-trehalose dihydrate | 5.500 |
| D-sorbitol | 3.750 |
| Tris | 0.073 |
| Urea | 0.250 |

Each freeze-dried material was rehydrated before titering with a 0.4% NaCl solution. 3 to 6 vials were titered so as to obtain an average titer.

Two titering techniques were used. The CCID50 technique is based on a series of dilutions of the dengue viral suspension, each diluted product is distributed into the wells of a 96-well plate containing Vero cells. After 7 days of culture, the Vero cells are fixed and stained when dengue virus is present after the use of monoclonal antibodies specific to each serotype. The infectious titer is calculated according to the number of positive wells, related to the dilution of the sample. The CCID50 is calculated by the least squares method, and the titer is expressed as log 10 CCID50/ml.

The pPFU technique is based on the same principle as the CCID50 technique. However, the titer is obtained by individual counting of the cytopathogenic effects. The analysis is carried out by image analysis. The titering is accurate to +/−0.3 log.

TABLE 2

Stability results for the freeze-dried material, expressed in the form of loss (log)

| Viral loss status | log | | | |
|---|---|---|---|---|
| freeze-dried material | CYD1 | CYD2 | CYD3 | CYD4 |
| Loss at freeze-drying | 0.2 | 0.2 | 0.2 | 0.3 |
| 7 days at 37° C. | 0.6 | 0.5 | 0.4 | 0.5 |
| 14 days at 37° C. | 0.9 | 0.9 | 0.8 | 0.9 |
| 1 month a 37° C. | 1.5 | 1.5 | 1.4 | 1.4 |
| 7 days at 45° C. | 1.1 | 1.2 | 1.1 | 1.2 |
| 14 days at 45° C. | 3.0 | 3.3 | 3.1 | 3.1 |

TABLE 3

Stability results for the rehydrated freeze-dried material, expressed in the form of loss (log)

| Viral loss status | log | | | |
|---|---|---|---|---|
| rehydrated | CYD1 | CYD2 | CYD3 | CYD4 |
| 6 h 5° C. | 0 | 0 | 0.1 | 0 |
| 1 h 25° c. | 0.1 | 0.1 | 0.1 | 0.3 |
| 4 h 25° C. | 0.3 | 0.3 | 0.3 | 0.5 |
| 2 h 36° C. | 0.4 | 0.5 | 0.6 | 0.7 |

Example 4

Stability of the Freeze-Dried, Stabilized Chimeric Yellow Fever-Dengue Bulk Tetravalent Vaccine Composition—Composition Different in Terms of Sugar, According to Example 1 and 2

The 7.5% sucrose/5.5% trehalose mixture was replaced with sucrose at 13%, the other components remaining unchanged.

TABLE 4

Stability results for the freeze-dried material, expressed in the form of loss (log)

| Viral loss status | log | | | |
|---|---|---|---|---|
| freeze-dried material | CYD1 | CYD2 | CYD3 | CYD4 |
| Loss at freeze-drying | 0 | 0 | 0.1 | 0.2 |
| 7 days a 37° C. | 0.6 | 0.8 | 0.6 | 0.6 |

TABLE 5

Stability results for the rehydrated freeze-dried material, expressed in the form of loss (log)

| Viral loss status | log | | | |
|---|---|---|---|---|
| rehydrated | CYD1 | CYD2 | CYD3 | CYD4 |
| 1 h 25° C. | 0.8 | 0.1 | 0.4 | 0.3 |
| 4 h 25° C. | 0.6 | 0.7 | 0.5 | 0.5 |

Example 5

Stability of the Freeze-Dried, Stabilized Chimeric Yellow Fever-Dengue Bulk Tetravalent Vaccine Composition—HEPES Buffer Composition, According to Examples 1 and 2

The Tris buffer was replaced with the HEPES buffer, at 0.36%, the other percentages of components of the stabilizer remaining unchanged.

TABLE 6

Stability results for the freeze-dried material, expressed in the form of loss (log)

| Viral loss status | log | | | |
|---|---|---|---|---|
| freeze-dried material | CYD1 | CYD2 | CYD3 | CYD4 |
| Loss at freeze-drying | 0.3 | 0.3 | 0.3 | 0.3 |
| 7 days at 37° C. | 0.6 | 0.5 | 0.7 | 0.7 |
| 14 days at 37° C. | 0.4 | 0.7 | 0.7 | 1.0 |

TABLE 7

Stability results for the rehydrated freeze-dried material, expressed in the form of loss (log)

| Viral loss status | log | | | |
|---|---|---|---|---|
| rehydrated | CYD1 | CYD2 | CYD3 | CYD4 |
| 1 h 25° C. | 0.1 | 0.2 | 0.3 | 0.2 |
| 4 h 25° C. | 0.3 | 0.1 | 0.5 | 0.5 |
| 2 h 36° C. | 0.2 | 0.1 | 0.3 | 0.2 |

Example 6

Stability of the Tetravalent Bulk Vaccine Composition in the Form of Freeze-Dried Microbeads This study compared the stability of the tetravalent bulk vaccine composition, produced as described in Example 1, dried either in the form of a freeze-dried material (Example 2) or in the form of freeze-dried microbeads. The freeze-dried microbeads were produced using the method illustrated in FIG. 1.

The bulk aqueous vaccine composition was formed into calibrated droplets by virtue of the "prilling" technology, which is based on the vibration of calibrated nozzles. These droplets subsequently freeze as they fall in a cryogenic chamber inside which the temperature was maintained below −110° C., either by direct injection of liquid nitrogen or by countercurrent sweeping of this very cold gas (temperature <−110° C.). Frozen calibrated beads thus obtained were distributed onto pre-cooled metal trays. These trays were then placed on the shelves, precooled to −50° C., of a freeze-drier such that the temperature of the frozen beads never exceeds their glass transition temperature at maximum cryoconcentration (Tg' which can be between −10° C. and −40° C.). This made it possible to avoid partial fusion, aggregation of the beads or recrystallization of certain excipients. Once the product had been placed in the freeze-drier, the apparatus was placed under vacuum in order to form the sublimation of ice, as for conventional freeze-drying of the product as defined by the prior art. For this application, the following desiccation parameters were applied:

Primary desiccation at a shelf temperature equal to −35° C. and a pressure equal to 50 μbar for 10 h.

Secondary desiccation at a shelf temperature equal to 20° C. and at a pressure equal to 50 μbar for 3 h.

FIG. 2 gives an indication as to the particle size of the beads obtained by means of this method.

The dry microbeads were collected in bulk so as to be analyzed and stored. The storage conditions were adapted for the storage of dry, friable and hygroscopic powders. When the microbeads were rehydrated with a diluent, reconstitution occurred instantaneously.

The residual water content of the products was measured by the Karl Fischer method as defined by the International Pharmacopoeia (4th Edition, Methods of Analysis: 2. Chemical methods: 2.8 Determination of water by the Karl Fischer method). The value obtained was less than 2%.

The beads obtained were subsequently dispensed so as to obtain the equivalent of one dose per vial. These vials were stored at 37° C. and at 45° C. in order to study the thermostability of this product and to compare it with that dried by conventional freeze-drying. The activity of the viruses was assayed by the pPFU technique and details of the results obtained are given in Tables 8 to 10 below:

TABLE 8

Initial titers for each serotype of the bulk aqueous vaccine composition before drying, expressed as log 10 PFU/dose:

| | CYD1 | CYD2 | CYD3 | CYD4 |
|---|---|---|---|---|
| Antigen titer in the bulk aqueous vaccine composition | 4.9 | 5.5 | 5.6 | 5.7 |

TABLE 9

Loss of activity for each serotype during drying in the form of microbeads, log10 PFU/dose:

| | CYD1 | CYD2 | CYD3 | CYD4 |
|---|---|---|---|---|
| Loss of infectious titer | 0.4 | 0.2 | 0.2 | 0.2 |

TABLE 10

Results of thermostability at 37° C. and at 45° C. for each serotype of the freeze-dried microbeads:

| | PFU/dose | | | |
|---|---|---|---|---|
| Loss of infectious titer | CYD1 | CYD2 | CYD3 | CYD4 |
| 7 days at 37° C. | 0.3 | 0.3 | 0.3 | 0.3 |
| 14 days at 37° C. | 0.6 | 0.5 | 0.6 | 0.6 |
| 1 month at 37° C. | 1.2 | 1.2 | 1.2 | 1.1 |
| 7 days at 45° C. | 0.9 | 0.8 | 0.9 | 0.8 |
| 14 days at 45° C. | 2.7 | 2.4 | 2.3 | 2.2 |

For each of the 4 serotypes, the losses during the drying process were equivalent between the freeze-drying (described in Examples 2 and 3) and the microbead method (between 0.2 and 0.4 log 10 PFU/dose). The dry form in microbead form exhibited better thermostability at 37° C. and at 45° C. than the standard freeze-dry form, with a difference of 0.3 log after 1 month at 37° C., which difference became accentuated and reached 0.8 log after 14 days of storage at 45° C.

Given that this difference in stability was observed with identical vaccine compositions, the operating conditions of the microbead method, and more particularly the rapid freezing phase, has a beneficial effect on the stability of the live chimeric viruses.

Example 7

Stability of the Freeze-Dried, Stabilized Chimeric Yellow Fever-West Nile Bulk Vaccine Composition, According to Examples 1 and 2

The stabilized, aqueous chimeric yellow fever-West Nile bulk vaccine composition was stabilized with the stabilizer of the present invention (according to Examples 1 and 2) before freeze-drying (according to Example 3) each vial into which 0.3 ml had been dispensed. The percentage of excipients of the stabilized freeze-dried vaccine composition is indicated in Table 1 of Example 3. In parallel, stabilized, aqueous chimeric yellow fever-West Nile bulk vaccine composition was stabilized with a reference stabilizer containing Human Serum Albumin (HSA) before freeze-drying each vial into which 0.3 ml had been dispensed Titers were measured using the PFU technique. The table below compares the stability profiles of the two stabilizer of the chimeric yellow fever-West Nile virus.

TABLE 6

Stability results of the chimeric yellow fever-West Nile virus for the freeze-dried material, expressed in the form of loss (log)

| | log | |
|---|---|---|
| Viral loss status freeze-dried material | Present invention stabilizer | Reference stabilizer with HSA |
| Loss at freeze-drying | 0.1 | 0.2 |
| 3 days at 37° C. | 0.2 | 0.2 |
| 7 days at 37° C. | 0.2 | 0.2 |
| 14 days at 37° C. | 0.3 | 0.4 |

All patents, patent application publications, and other reference publications cited above are incorporated herein by reference. Other embodiments are within the following claims.

What is claimed is:

1. A stabilizer for compositions comprising one or more live attenuated flaviviruses, which comprises, in an aqueous solution without proteins of animal origin and without added salts having divalent cations,
   a buffer,
   2.5% to 6.5% of sorbitol,
   2.5% to 13% of sucrose,
   0 to 7.5% of trehalose and/or 0 to 7.5% of a disaccharide other than sucrose or trehalose or a trisaccharide,
   0.2% to 0.5% of urea,
   0.8% to 2.5% of an amino acid mixture comprising arginine (Arg), cystine (Cys-Cys), histidine (His), isoleucine (Ile), leucine (Leu), lysine (Lys), methionine (Met), phenylalanine (Phe), threonine (Thr), tryptophan (Trp), tyrosine (Tyr), valine (Val), alanine (Ala), asparagine (Asn), aspartic acid (Asp), glutamic acid (Glu), glycine (Gly), proline (Pro) and serine (Ser).

2. The stabilizer as claimed in claim 1, which comprises one or more buffers selected from the group consisting of TRIS (tris(hydroxymethyl)-aminomethane), HEPES (2-(4-(2-hydroxyethyl)-1-piperazinyl)ethane-sulfonic acid) and potassium phosphate and/or sodium phosphate.

3. The stabilizer as claimed in claim 2, wherein the TRIS is present at a concentration of from 5 to 10 mM.

4. The stabilizer as claimed in claim 2, wherein the HEPES is present at a concentration of from 7.5 to 20 mM.

5. The stabilizer as claimed in claim 1, comprising
   3.8% (w/v) of sorbitol,
   7.5% (w/v) of sucrose,
   5.5% (w/v) of trehalose,
   0.25% (w/v) of urea and
   1.5% (w/v) of the amino acid mixture.

6. A stabilized bulk aqueous vaccine composition comprising one or more live attenuated flaviviruses and the stabilizer as claimed in claim 1.

7. The vaccine composition as claimed in claim 6, which comprises one or more live attenuated dengue (DEN) virus serotypes.

8. The vaccine composition as claimed in claim 6, which comprises live attenuated yellow fever (YF) viruses.

9. The vaccine composition as claimed in claim 6, which comprises live attenuated West Nile (WN) virus disease viruses.

10. The vaccine composition as claimed in claim 6, which comprises live attenuated Japanese encephalitis (JE) viruses.

11. The vaccine composition as claimed in claim 6, which comprises one or more chimeric live attenuated flaviviruses.

12. The vaccine composition as claimed in claim 11, which comprises one or more serotypes of a chimeric YF-DEN (yellow fever-dengue) virus.

13. The vaccine composition as claimed in claim 11, which comprises a chimeric YF-WN (yellow fever-West Nile virus) virus.

14. The vaccine composition as claimed in claim 11, which comprises a chimeric YF-JE (yellow fever-Japanese encephalitis) virus.

15. A method for stabilizing one or more live attenuated flaviviruses, comprising diluting a purified and concentrated viral harvest comprising one or more live attenuated flaviviruses by adding stabilizer so as to obtain the final concentrations of the stabilizer defined according to claim 1 in order to obtain a stabilized bulk aqueous vaccine composition comprising said one or more live attenuated flaviviruses.

16. The stabilization method as claimed in claim 15, comprising drying the aqueous composition by means of a method selected from the group of foam-drying, spray-drying or freeze-foam-drying.

17. The stabilization method as claimed in claim 15, comprising drying the aqueous composition by means of freeze-drying method.

18. The stabilization method as claimed in claim 15, comprising drying the aqueous composition by means of spray-freeze-drying method.

19. The stabilization method as claimed in claim 17, wherein, in a first step, the aqueous solution is frozen in the form of uniform particles or of beads, and wherein, in a second step, the frozen uniform particles or beads are subjected to drying in order to obtain a stabilized dry product in the form of uniform particles or of beads.

20. The stabilization method as claimed in claim 19, wherein the uniform particles or beads of the stabilized dry product have a diameter of approximately 100 µm to 1500 µm.

21. The stabilization method as claimed in claim 20, wherein the uniform particles or beads of the stabilized dry product have a diameter of approximately 500 µm to 1000 µm.

22. A dry vaccine composition obtained by drying the stabilized bulk composition as claimed in claim 6.

23. The dry vaccine composition as claimed in claim 22, which is present in the form of uniform particles or of beads.

24. The dry vaccine composition as claimed in claim 23, wherein each particle or each bead contains a mixture of various live attenuated and/or chimeric live attenuated flaviviruses.

25. The dry vaccine composition as claimed in claim 23, wherein each particle or each bead contains live attenuated and/or chimeric live attenuated flaviviruses of a single type.

26. A method for preparing a vaccine, comprising the step of reconstituting the composition as claimed in claim 22 with an aqueous solution.

27. A flaviviral vaccine kit comprising a first container containing the dry vaccine composition as claimed in claim 22 and a second container containing an aqueous solution for reconstituting the vaccine.

28. The kit as claimed in claim 27, wherein each particle or bead of the dry vaccine composition in the first container contains a mixture of various live attenuated and/or chimeric live attenuated flaviviruses.

* * * * *

UNITED STATES PATENT AND TRADEMARK OFFICE
CERTIFICATE OF CORRECTION

PATENT NO. : 8,142,795 B2
APPLICATION NO. : 12/500156
DATED : March 27, 2012
INVENTOR(S) : Françon et al.

It is certified that error appears in the above-identified patent and that said Letters Patent is hereby corrected as shown below:

Column 2, Line 48, replace "Examples ofYF17D" with --Examples of YF17D--.

Column 2, Line 49, replace "YE-Vax®" with --YF-Vax®--.

Column 5, Line 55, replace "beak-up" with --break-up--.

Column 9, Line 63, replace "The pPFU technique" with --The µPFU technique--.

Column 12, Line 22, replace "the pPFU technique" with --the µPFU technique--.

Signed and Sealed this
Twelfth Day of March, 2013

Teresa Stanek Rea
*Acting Director of the United States Patent and Trademark Office*

UNITED STATES PATENT AND TRADEMARK OFFICE

(12)    CERTIFICATE EXTENDING PATENT TERM
        UNDER 35 U.S.C. § 156

| | | | |
|---|---|---|---|
| (68) | PATENT NO. | : | 8,142,795 |
| (45) | ISSUED | : | March 27, 2012 |
| (75) | INVENTOR | : | Françon et al. |
| (73) | PATENT OWNER | : | Sanofi Pasteur |
| (95) | PRODUCT | : | DENGVAXIA® (Dengue Tetravalent Vaccine, Live) |

This is to certify that an application under 35 U.S.C. § 156 has been filed in the United States Patent and Trademark Office, requesting extension of the term of U.S. Patent No. 8,142,795 based upon the regulatory review of the product DENGVAXIA® (Dengue Tetravalent Vaccine, Live) by the Food and Drug Administration. According to United States Patent and Trademark Office records, the original expiration date of the patent as of the date of issuance of this certificate is November 30, 2029. Because it appears that the requirements of the law have been met, this certificate extends the term of the patent for the period of

(94)                              1,248 days subject to the payment of maintenance fees as provided by law, with all rights pertaining thereto as provided by 35 U.S.C. § 156.

I have caused the seal of the United States Patent and Trademark Office to be affixed this 15th day of February 2023.

Kathi Vidal

Katherine K. Vidal
Under Secretary of Commerce for Intellectual Property and Director of the United States Patent and Trademark Office